US00PP34278P2

(12) United States Plant Patent
Hansen

(10) Patent No.: US PP34,278 P2
(45) Date of Patent: May 31, 2022

(54) ***VERONICA* PLANT NAMED 'PURPLE LEIA'**

(50) Latin Name: ***Veronica spicata* L.**
Varietal Denomination: Purple Leia

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,086

(22) Filed: Feb. 1, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68; A01H 5/02
See application file for complete search history.

*Primary Examiner* — Keith O. Robinson

(57) ABSTRACT

The new and distinct cultivar of ornamental Spike Speedwell plant, *Veronica spicata* 'Purple Leia', with medium to tall height, stiff, upright, heavily-branched, dense spikes of rosy-purple flowers beginning in early summer and continuing for at least five weeks above deep green foliage. The new plant is useful in the landscape as a specimen, en masse, as a container plant or as a cut flower.

1 Drawing Sheet

Botanical classification: *Veronica spicata* L.
Variety denomination: 'Purple Leia'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Feb. 1, 2021 followed by the "Walters Gardens 2021-2022 Catalog" with a brief description and photograph first distributed on May 21, 2021. Prior to that the claimed plant was first sold on Jul. 12, 2021 by Walters Gardens, Inc., who obtained the plant and all information relating thereto, from the inventor. No plants of *Veronica* 'Purple Leia' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Spike Speedwell, botanically known as *Veronica spicata* 'Purple Leia', and hereinafter referred to as the cultivar 'Purple Leia' or the "new plant". The new plant was crossed by the inventor on Jun. 27, 2016 in the hybridizing greenhouses of a wholesale perennial nursery in Zeeland, Mich., USA. The female or seed parent was a proprietary unreleased hybrid known only by the breeder code 13-33-5 (not patented) and the male or pollen parent was a proprietary unreleased hybrid known only by the breeder code 13-32-10 (not patented).

The new plant was assigned the breeder code of 16-7-1. 'Purple Leia' has been asexually propagated initially division and later by basal cuttings and shoot tip tissue culture at the same nursery in the greenhouses in Zeeland, Mich., since the summer of 2018 with subsequent asexually propagated plants found to be identical to the original selection with all the same traits as the original seedling.

BRIEF SUMMARY OF THE PLANT

*Veronica* 'Purple Leia' is unique from all other Spike Speedwell known to the inventor. Several other cultivars may have some similar traits, but this is the only variety known by the inventor to have the following characteristic combinations that establish the new plant as unique:

1. Medium to tall habit with stiff, upright, spikes above dense stems of deep green foliage.
2. Scapes with numerous, dense flowers of rosy-purple petals.
3. Heavily-branched peduncles begin blooming in early summer and continue for at least five weeks into summer.

The closest comparison varieties known to the inventor are 'Mona Lisa Smile' U.S. Plant Pat. No. 30,477, 'Purpleicious' U.S. Plant Pat. No. 17,639, 'Hocus Pocus' U.S. Plant Pat. No. 23,853, 'Blue Skywalker' U.S. Plant Pat. No. 29,406, 'Lavender Lightsaber' U.S. Plant Pat. No. 32,359, 'Purple Illusion' U.S. Plant Pat. No. 31,301 and 'Purple Explosion' U.S. Plant Pat. No. 24,757.

'Mona Lisa Smile' is smaller in habit and has a flower color that is a strong purplish-red. 'Purpleicious' has flowers that are lighter violet-purple and the habit is smaller with peduncles less branched. 'Hocus Pocus' has a smaller habit and size, and the flowers are a darker-purple. 'Blue Skywalker' has a similar habit and size, but the flowers are a lavender-blue. 'Lavender Lightsaber' has a similar habit and size, but the flower color is a soft lavender. 'Purple Illusion' has a smaller habit with fewer flowers per stem. 'Purple Explosion' is taller in habit with less branching and fewer flowers per stem.

The female parent, 13-33-5, is shorter and the flower was a darker shade of lavender purple. The male parent, 13-32-10, has lighter shade of lilac-lavender flowers with a taller habit.

BRIEF DESCRIPTION OF THE DRAWINGS

The photographs of the new plant demonstrate the overall appearance and unique traits of 'Purple Leia' as a two-year-old plant grown in a full-sun display garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
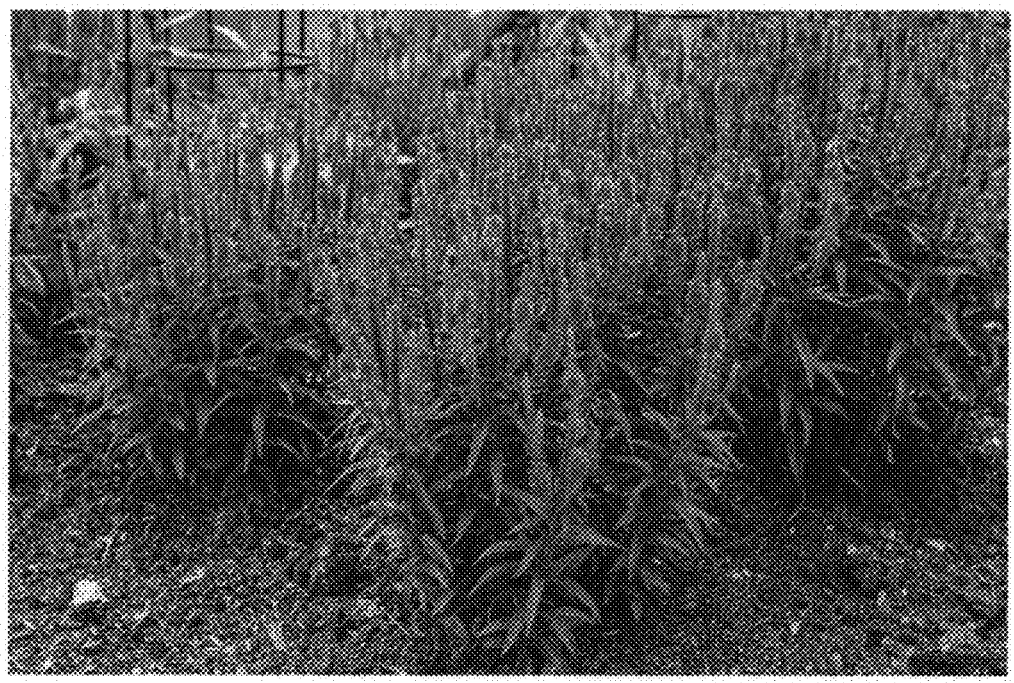
FIG. 1 shows the habit of the new plant in full flower.
Figure 2:
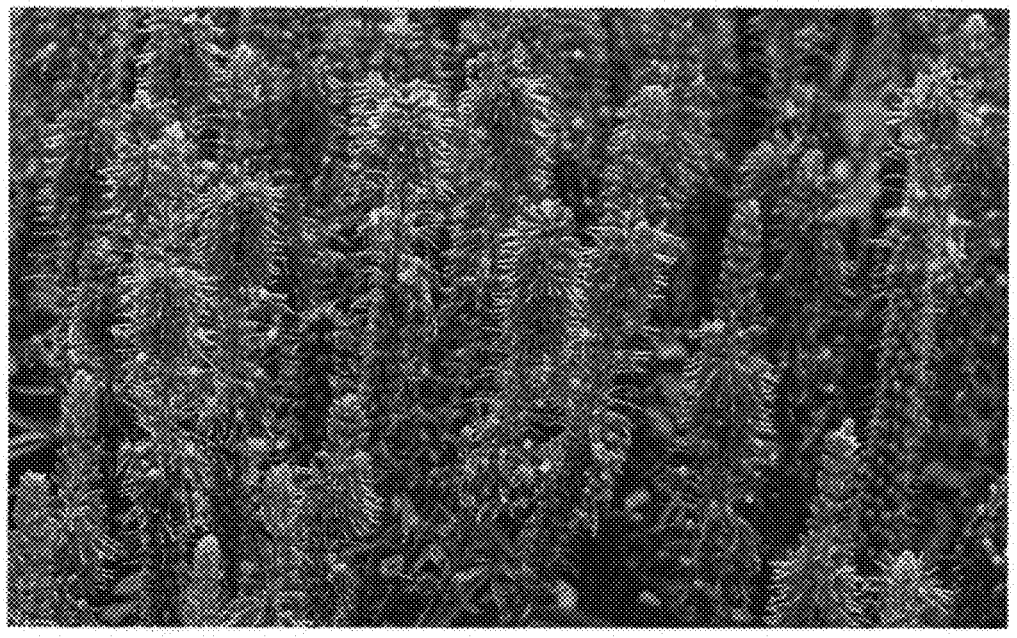
FIG. 2 shows a close-up of the flowers and buds.

The following descriptions and color references of *Veronica* 'Purple Leia' are based on the 2015 edition of The Royal Horticultural Society Colour Chart except where common dictionary terms are used. 'Purple Leia' has not been observed under all possible environments. The phenotype may vary slightly with different growing environments such as temperature, light, fertility, soil pH, moisture and maturity levels, but without any change in the genotype. The following observations and size descriptions are based on two-year-old plants grown in a full-sun display garden of a nursery in Zeeland, Mich.

Botanical classification: *Veronica spicata;*

Parentage: The female (seed parent) was 13-33-5; the male or pollen parent was 13-32-10 a selection comprising 'Purpleicious', 'Sweet Lullaby U.S. Plant Pat. No. 23,611 and 'Lilac' (not patented);

Propagation: The plant roots from cuttings in about 2 weeks and finishes to flowering in a 3.8-liter container in 8 to 10 weeks following a vernalization period of about 8 weeks;

Roots: Fibrous; heavily branching; color between RHS 164C and RHS 164D;

Plant habit: Hardy herbaceous perennial; compact; with about 20 stems; main stems branching in distal portion; to about 70 cm tall and clumping to about 55 cm wide; flowering beginning late spring in Michigan and continuing for up to 5 weeks;

Leaves: Simple; flat; lanceolate; opposite; margin ciliolate, serrated with teeth 3.0 mm apart and 1.0 mm long; micro-puberulent adaxial and glabrous between veins abaxial, lustrous adaxial and matte abaxial; acute apex; distal leaves with attenuate base and proximal leaves with rounded base; to about 11 cm long by 3 cm wide near middle, average about 8 cm long and 2.5 cm wide, decreasing in both length and width distally; about 16 leaves per stem;

Leaf color: Mature adaxial nearest RHS NN137A, abaxial nearest RHS 138A; young expanding adaxial between RHS 145A and RHS 146D, abaxial nearest RHS 144A;

Veins: Pinnate, abaxial midrib costate; sparsely puberulent abaxial midrib and glabrate to glabrous adaxial and abaxial veins;

Vein color: Adaxial midrib and proximal lateral veins nearest RHS 146C; abaxial midrib nearest RHS 146D and lateral veins nearest RHS 137B;

Petiole: Simple; concavo-convex; glabrous adaxial and abaxial; margin micro-ciliolate; base slightly clasping; to about 12 mm long and 5 mm wide at base, decreasing distally to an average about 6 mm long and 3.5 mm wide;

Petiole color: Adaxial nearest RHS 146B; abaxial sides nearest RHS 137C and midrib nearest RHS 146D;

Stem: Cylindrical; puberulent; length about 45 cm before flowers, diameter about 3.0 mm at base; color nearest RHS 146C;

Internodes: 12 below flowers; average about 3.7 cm apart; node color nearest RHS 138A;

Inflorescence: Heavily branched; upright spikes in compressed conglomerate; about 12 cm long and 4.5 cm wide with up to six lateral branches per stem; with about 550 flowers per center stem, to 330 flowers per branch and about 1400 per branched peduncle;

Flower bud one to two days prior to opening: Convolute; oblong; rounded base and apex; glabrous; about 4.0 mm long and 2.0 mm diameter;

Flower bud color one to two days prior to opening: Nearest RHS 77A with calyxes nearest RHS 138A;

Flowers: Zygomorphic, perfect, complete; about 6.0 mm wide, 6.0 mm tall and about 8.0 mm long to exserted anthers; corolla about 6.0 mm across and about 4.5 mm long; corolla tube fused in basal 2.0 mm and 1.7 mm diameter near base; flowers persist individually for 4 to 6 days whether on the plant or cut; petals self-cleaning, sepals and style persistent; attitude outwardly;

Flower fragrance: Not detectible;

Flower timing: Late spring and continuing for about five weeks;

Petals: Four; one slightly larger petal above, two on either side, one slightly smaller below; rounded apices; entire; glabrous adaxial and abaxial except basal 2.0 mm adaxial of fused tube with pubescent tuft; fused in basal 2.0 mm; larger top and side petals about 4.5 mm long by 6.0 mm wide, smaller lower petal about 6.0 mm long and 3.5 mm wide;

Petal color: Abaxial and adaxial nearest RHS N81B with corolla tube base nearest RHS NN155D; adaxial tuft of hairs nearest RHS NN155D;

Androecium:

*Filaments*.—Two; divergent; glabrous; epipetalous about 1 mm from base; about 8 mm long by 0.3 mm; color nearest RHS N82B distally becoming white, RHS NN155D proximally.

*Anther*.—Dorsifixed, longitudinal; ellipsoidal; with acute rounded becoming acute, base rounded; about 2.0 mm long and 1.0 mm wide; ventral color nearest RHS N77B and dorsal nearest RHS N81B, nearest RHS 202A abaxial after pollen dehiscence.

*Pollen*.—Abundant, globose, less than 0.1 mm; nearest RHS 18C.

Gynoecium: One, superior; exserted; persists after petal drop;

*Style*.—Cylindrical; straight; attitude outwardly to slightly drooping; about 6.0 mm long by 0.5 mm; color nearest RHS N81B.

*Stigma*.—Globose; about 0.3 mm in diameter; color RHS 76B.

*Ovary*.—Globose to ellipsoid; about 1.2 mm long and 1.0 mm across; color nearest RHS 146D.

Calyx: Campanulate; 2.0 mm long and 2.5 mm diameter;

Sepals: Four; lanceolate; adaxial dull, glabrous; abaxial microscopically puberulent; acute apex; basal 1.5 mm fused forming campanulate calyx; margin entire, micro-ciliolate; to about 2.5 mm long and 1 mm wide;

Sepal color: Adaxial nearest RHS 138A, abaxial nearest RHS 137A;

Peduncle: About 20 per plant; raceme, strong, virgate, branched at upper nodes; cylindrical; pubescent distally to glabrescent proximally; flowering portion to about 24.5 cm long, about 20 cm across with branches and central stem portion about 18 mm wide;

Peduncle color: Nearest RHS 146C;

Pedicel: Rigid; cylindrical; micro-puberulent; about 1.7 mm long and 0.5 mm wide, attitude semi-upright;

Pedicel color: Nearest RHS 138B;

Bract: One; subtending each flower; linear; narrowly acute apex; entire; sessile attenuate base; glabrous adaxial and abaxial; proximal bracts about 15.0 mm long and 22 mm wide and decreasing distally to about 3.0 mm long and less than 1.0 mm wide;

Bract color: Nearest RHS 139A adaxial and nearest RHS 137A abaxial;

Fruit: Four-chambered, longitudinally-dehiscent capsule; ellipsoid with rounded apex and base, about 2.5 mm long and 2.0 mm across; color upon drying between RHS 199D and RHS 161C;

Seed: Prolific; typically about 2 to 4 per capsule; slightly flattened ellipsoidal; about 0.7 mm long and 0.5 mm across; color variable, nearest both RHS N199B and RHS N199C;

Growth: The new plant grows best with plenty of moisture and adequate drainage but is able to tolerate some drought when mature.

Hardiness: Hardiness at least from USDA zone 4 through 8.

Disease and pest resistance: Disease and pest resistance and susceptibility beyond what is typical of that of other Spike Speedwell has not been observed.

I claim:

1. A new and distinct cultivar of ornamental Spike Speedwell plant, *Veronica spicata* 'Purple Leia', as herein described and illustrated.

* * * * *